US00PP31853P3

(12) United States Plant Patent
Beatson

(10) Patent No.: US PP31,853 P3
(45) Date of Patent: Jun. 9, 2020

(54) HOP PLANT NAMED 'HORT4337'

(50) Latin Name: ***Humulus lupulus* L.**
Varietal Denomination: Hort4337

(71) Applicant: New Zealand Hops Limited, Nelson (NZ)

(72) Inventor: Ron Beatson, Motueka (NZ)

(73) Assignee: New Zealand Hops Limited, Nelson (NZ)

( * ) Notice: Subject to any disclaimer, the term of this patent is extended or adjusted under 35 U.S.C. 154(b) by 0 days.

(21) Appl. No.: 16/350,410

(22) Filed: Nov. 13, 2018

(65) Prior Publication Data

US 2019/0150343 P1 May 16, 2019

Related U.S. Application Data

(60) Provisional application No. 62/587,047, filed on Nov. 16, 2017.

(51) Int. Cl.
*A01H 5/00* (2018.01)
*A01H 6/00* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 5/02
See application file for complete search history.

*Primary Examiner* — Kent L Bell
(74) *Attorney, Agent, or Firm* — Leydig, Voit & Mayer, Ltd.

(57) ABSTRACT

A new and distinct hop plant is described. The new cultivar results out of selection from a population of seedlings derived from deliberate crossing tetraploid 00.L125-09 (seed parent) (not patented) and diploid 99-59-39 (pollen parent) (not patented). The new cultivar, 'Hort4337', is characterised by having cones which are mid-season maturing and having medium alpha acid content. The new cultivar is suitable for beer flavouring.

5 Drawing Sheets

Genus and species of plant claimed: *Humulus lupulus* L.
Variety denomination: 'Hort4337'.

BACKGROUND OF THE INVENTION

The new cultivar of hop, *Humulus lupulus* L., was created in the course of a planned breeding program carried out at Motueka, New Zealand. It was selected from a population of seedlings derived from crossing tetraploid 00.L125-09 (seed parent) (not patented) and diploid 99-59-39 (pollen parent) (not patented). The cross was carried out in 2004. Seedlings from the cross were grown in a nursery at the same location during the 2004-5 season and subsequently planted in the field in 2005-06 season. In 2006, 'Hort4337' was identified as having potential as a new cultivar and given the breeder code 04.43-37. The cultivar was selected on the basis of its good agronomic performance, and chemistry profile and because it imparts good flavour and aroma characteristics in beer. In 2011-12, 'Hort4337' was asexually propagated via rhizome cuttings at Motueka, New Zealand. The resulting plants were found to be true to type demonstrating that the characteristics of the new cultivar 'Hort4337' are stable and transmitted without change through succeeding generations.

SUMMARY OF THE INVENTION

A new and distinct hop plant is described. 'Hort4337' cultivar is characterised by having cones which are mid-season maturing and medium alpha acid content. The new cultivar is suitable for beer flavouring.

In 2011-12, 'Hort4337' was asexually propagated via rhizome cuttings at Motueka, New Zealand. The resulting plants were found to be true to type demonstrating that the characteristics of the new cultivar 'Hort4337' are stable and transmitted without change through succeeding generations.

For two seasons, from 2012/13 to 2013/14 'Hort4337' was evaluated in a replicated plot trial, for its commercial potential. In the winter of 2014 it was decided to advance 'Hort4337' due to its agronomic and chemistry properties for further testing including brewing trials. Brewing trials were conducted in the 2015-2016 and 2016-17 seasons.

'Hort4337' is maintained at Motueka, New Zealand, where it has undergone observations for uniformity. All plants have been found to be true to type, that is, no off types have been observed. 'Hort4337' is distinguished from its female parent, 00.L125-09 as 'Hort4337' is a triploid and has a much lower seed content around 1-2% w/w compared with 00.L125-09, a tetraploid which has >10% w/w seed content. The pollen parent, 99-59-39, is a male and thus does not produce cones.

Under New Zealand growing conditions 'Hort4337' is distinguished from varieties of common knowledge by the following characteristics: When compared to 'Pacific Jade™' (not patented), Waimea™ ('Hort3953') (US Plant Pat. No. 25,658), 'Rakau™' (not patented), 'Dr Rudi' (not patented) and 'Sticklebract' (not patented), 'Hort4337' has cones that mature earlier. In addition, 'Hort4337' typically has smaller cones than Waimea ('Hort3953') and 'Pacific Jade™' and the foliage of 'Hort4337' is more dense than the foliage of 'Southern Cross' (not patented).

BRIEF DESCRIPTION OF THE DRAWINGS

The accompanying photographs show typical specimens of the plant habit, cones, and leaves of the new cultivar as depicted in colours as nearly true as is reasonably possible to make the same in colour illustration of this character. The plants shown in these photographs were two years old.

DETAILED DESCRIPTION

Figure 1:
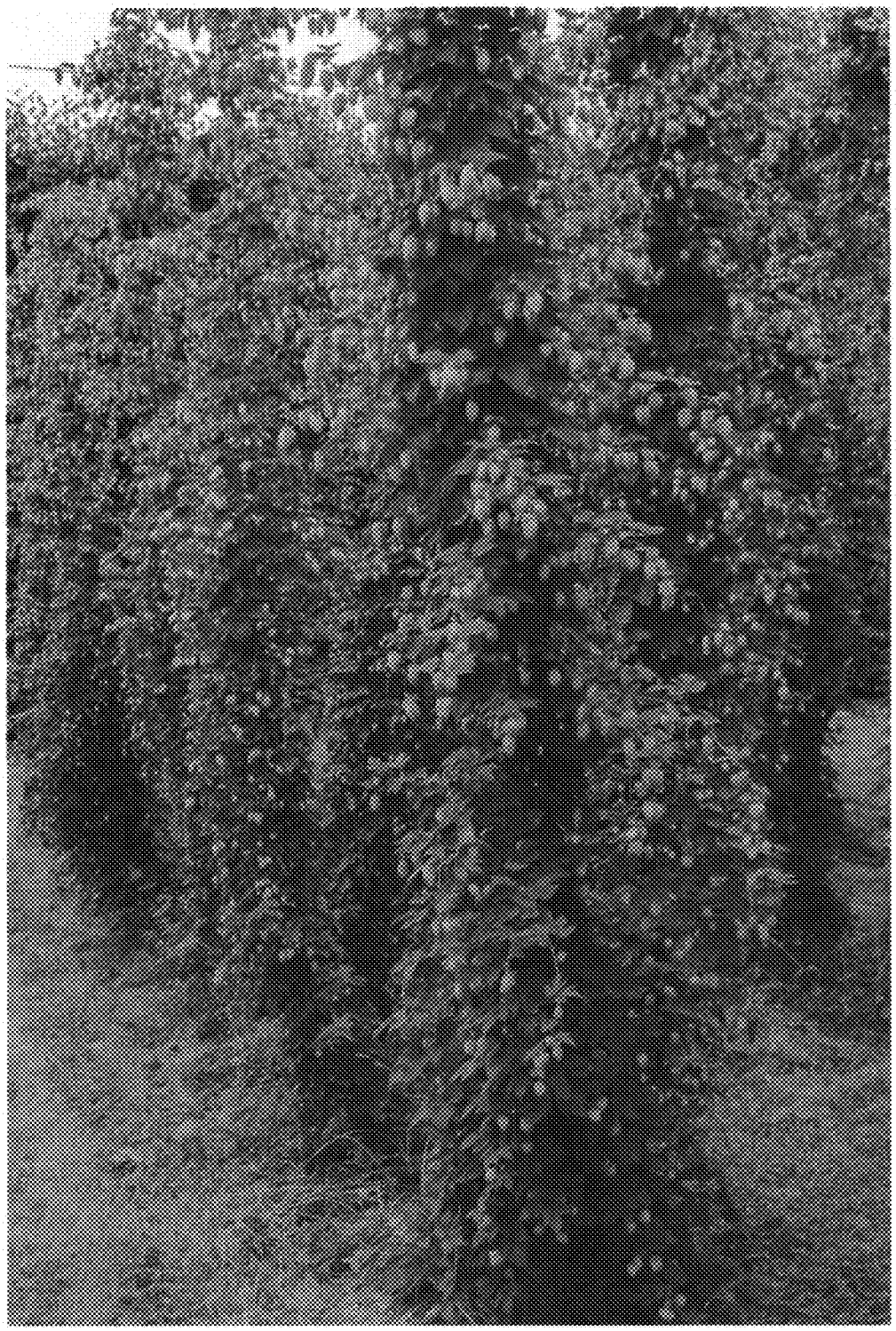
FIG. 1: A 'Hort4337' mature plant.
Figure 2:
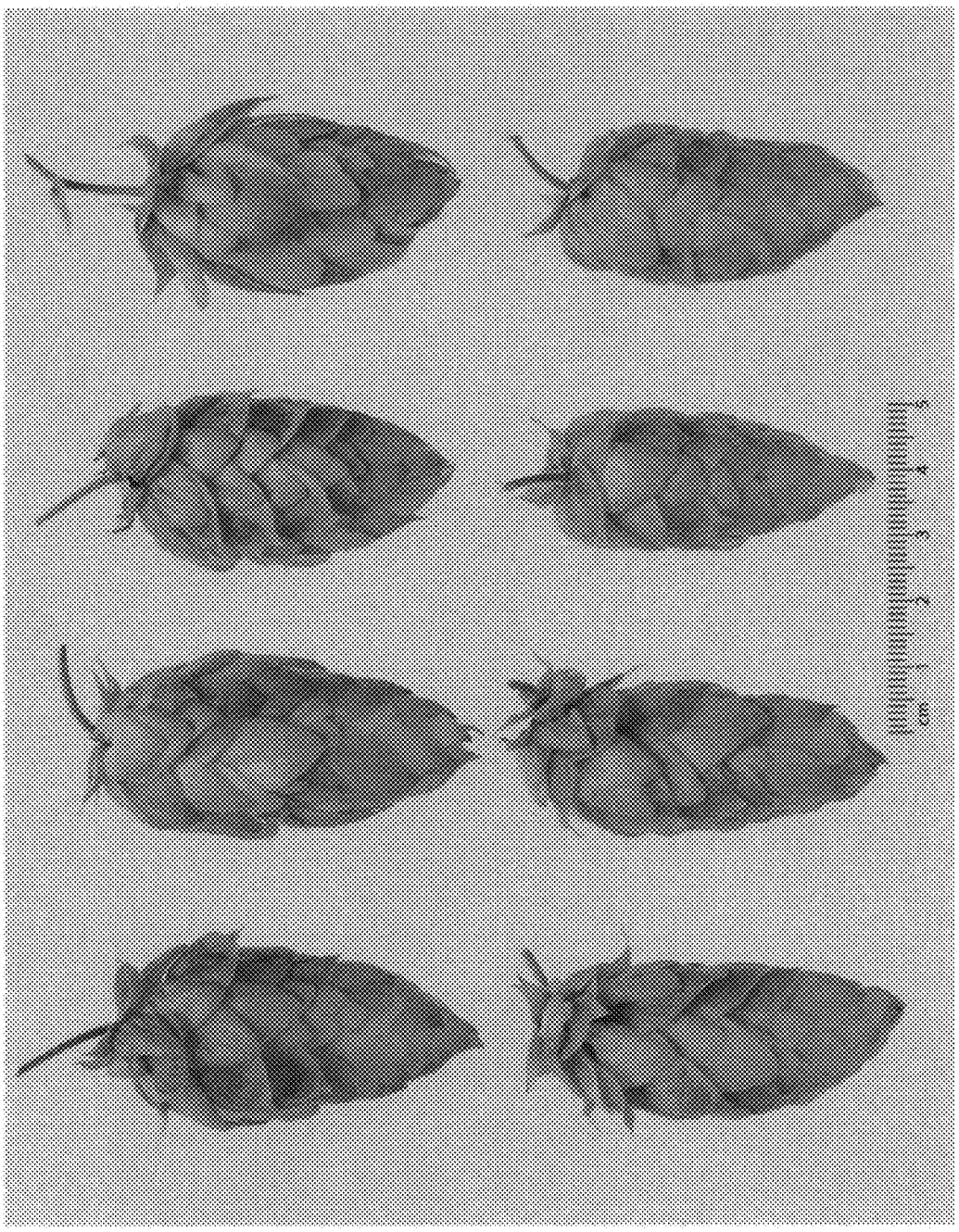
FIG. 2: 'Hort4337' cones in the studio.
Figure 3:
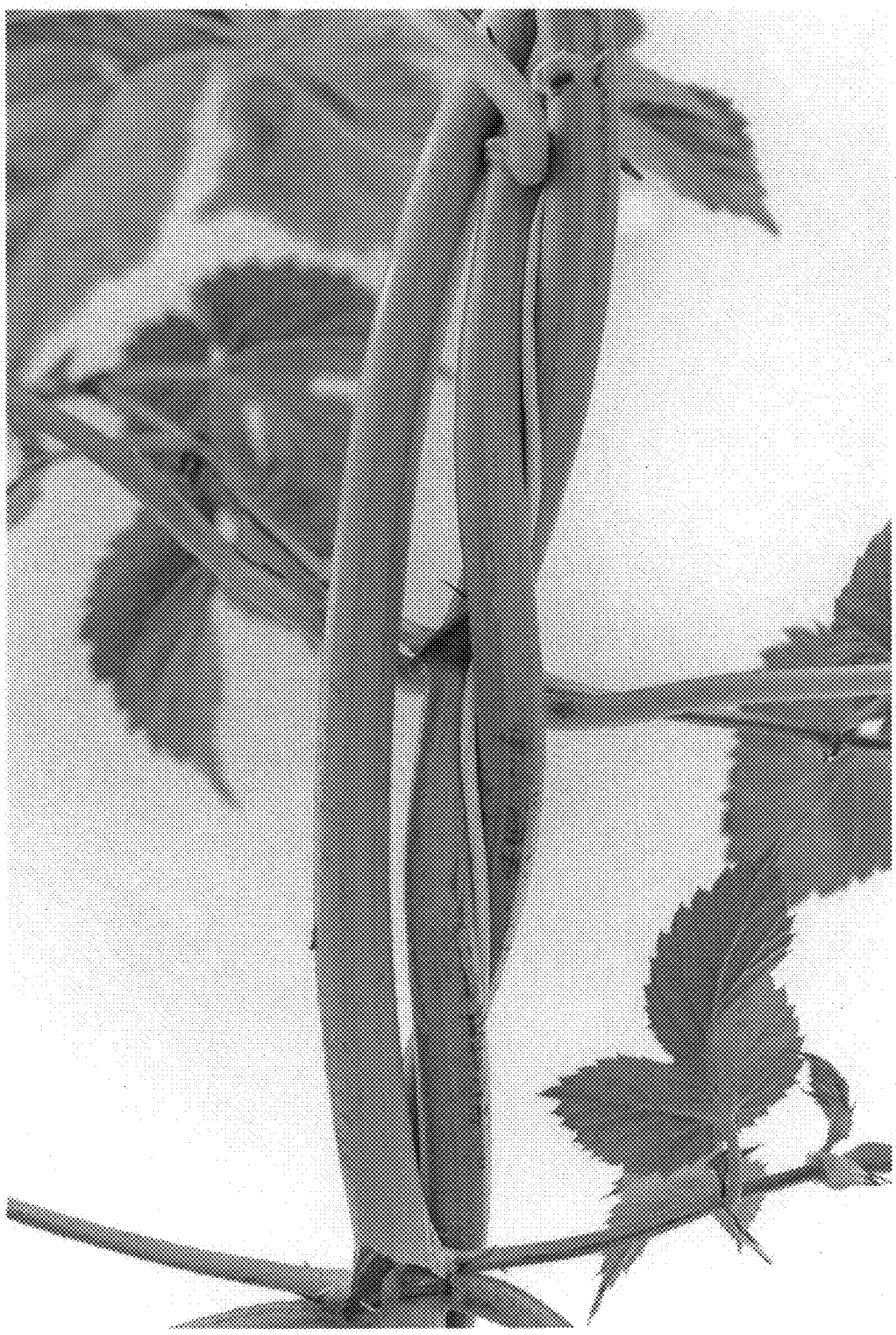
FIG. 3: 'Hort4337' stems.
Figure 4:
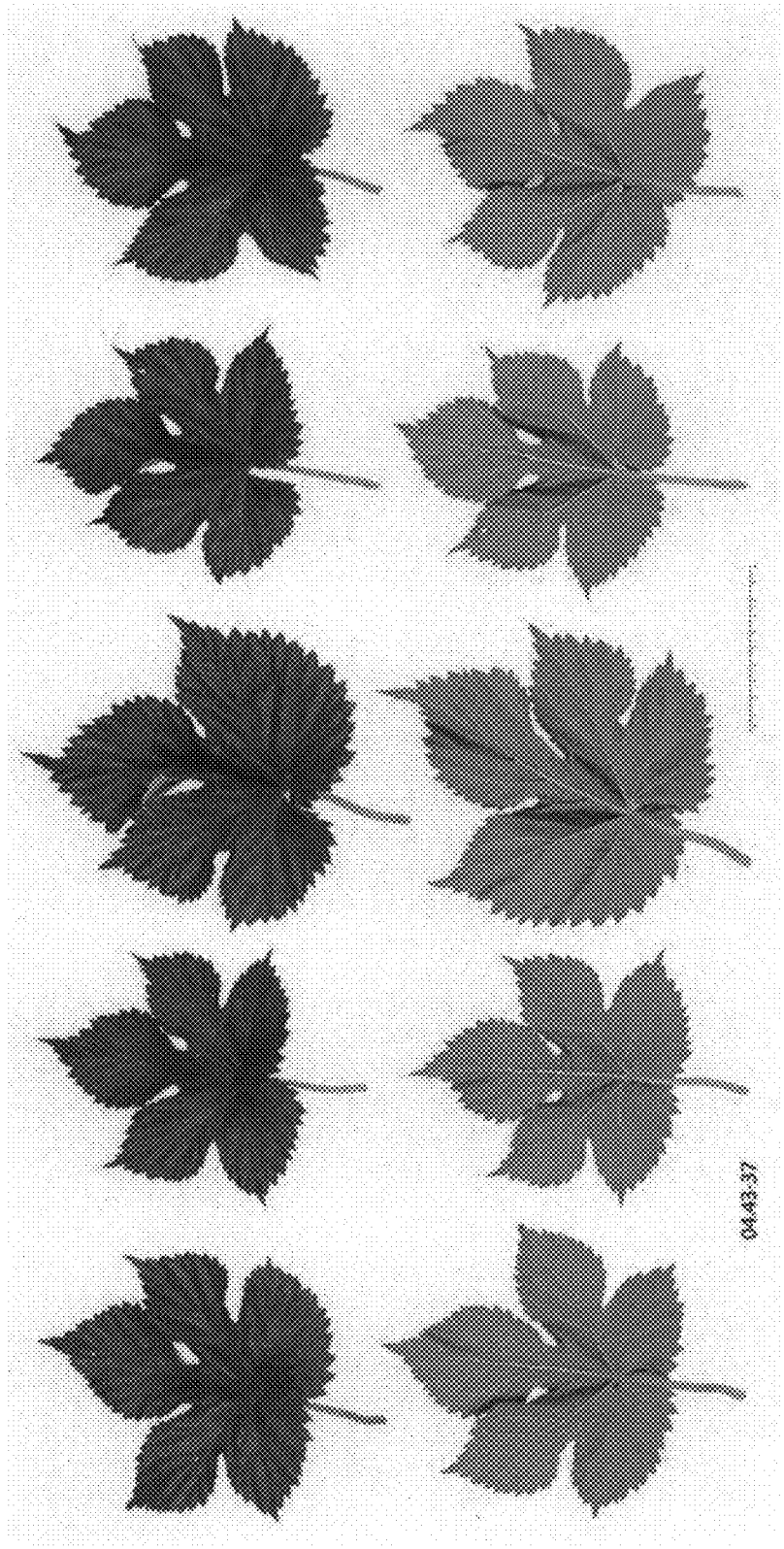
FIG. 4: Upper and underside of 'Hort4337' leaves.
Figure 5:
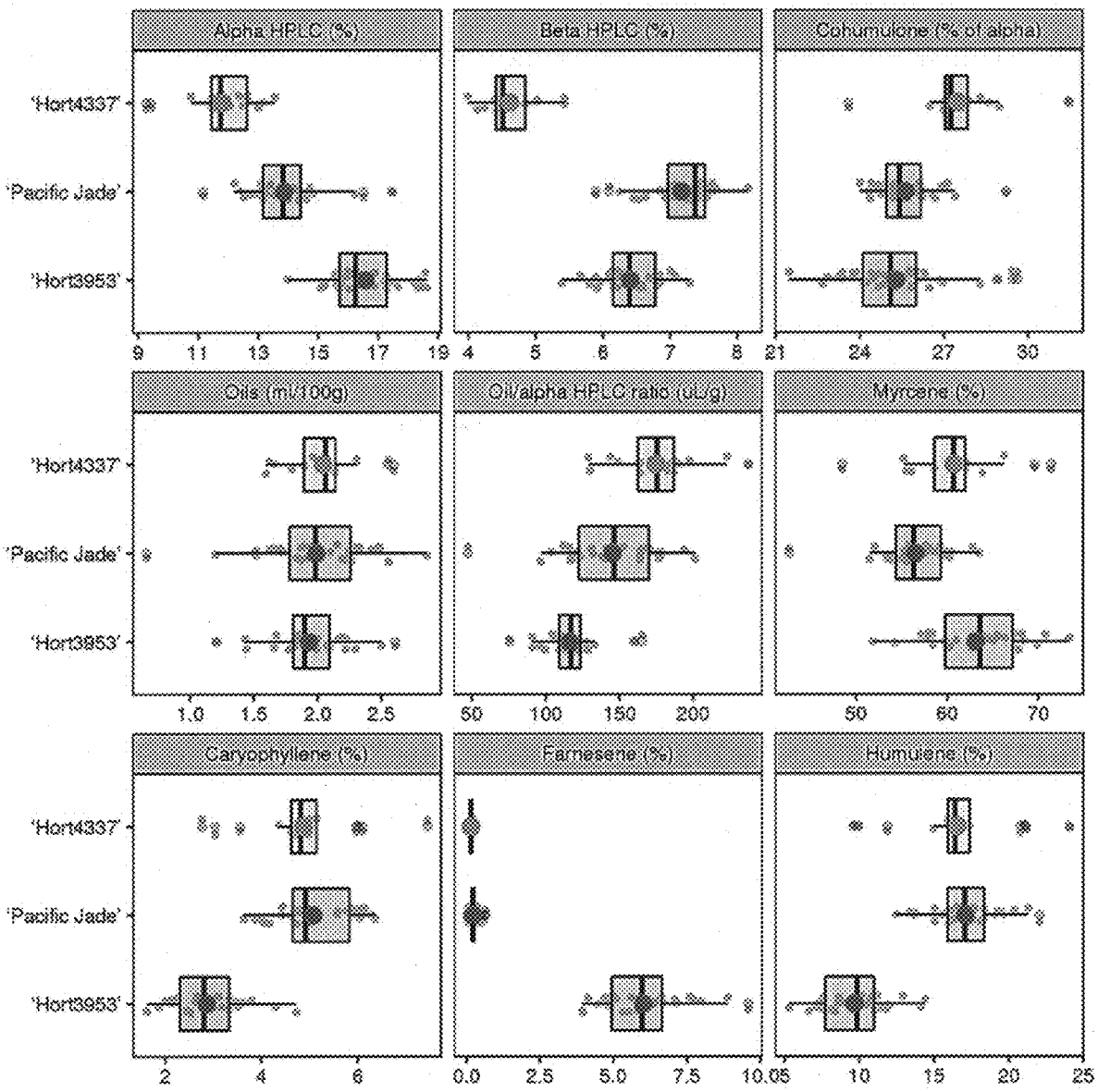
FIG. 5: Mean of at harvest chemistry profiles for 'Hort4337' and cultivars 'Pacific Jade™' and 'Hort3953' (Waimea™). Trials and testing were conducted in Motueka, New Zealand.

The following is a description of the new cultivar with colour terminology in accordance with The Royal Horticultural Society Colour Charts (R.H.S.C.C.) 2001 edition. The specimens described were two years old and were grown at Motueka, New Zealand. The observations were made over the 2014-2017 seasons.

Plant form and vigour: Mature plants had a normal growth type and produced a yield (averaging 2.2-2.6 tonnes/ha,) of mid-season maturing cones. The shape of the plant tended to be cylindrical to club shaped with the head being high volume. The main shoot of a one year old plant had an average vine diameter half way up the vine of 12 mm, and anthocyanin coloration was absent or very weak. Node pubescence was weak. The average internode length was 280 mm. Internode bine length was 28 cm and bine colour was 138B.

Laterals: The attitude of the laterals was pendant. The side shoots from the middle third of the plant were long in length, averaged 90 cm, and produced a high number of cones, an average of 7 per node. The side shoots from the top third of the plant had an average length of 100 cm and produced an average of 69 cones/node. Stipule pose is drooping, stipule colour is 144A, and the number of stipules per node is 2.

Leaves: The leaves were strongly lobed with predominantly five lobes. The large, weakly blistered leaves were alternate with crenate margins. The average leaf length was 183 mm and average width was 165 mm. The upper leaf surface colour was near, Green, 139A with light-medium intensity. The lower leaf surface colour was N138B. Venation pattern is palmatifid and venation colour is 145A. Petioles have an average length of 70 mm, an average width of 4.5 mm, and are near red purple 59A.

Cones: Were medium-large in size and narrow-ovate in shape in longitudinal section; in cross section they were square in shape. The cone average length was 48 mm and average width 22 mm. Bracts were large in size, with an average length of 20 mm and average width 12 m, Green in colour, near 143B. The bracts were slightly open and the bract apex was long in length. The shape of the tip of the bract is cuspidate. Bracteole had an average length of 16 mm and average width 10 mm. Bracteole shape was ovate, and the color of the bracteole was N144A. Strigs were medium length, and had an average length of 38 mm, with an average width of 3 mm. The colour of the strig was Green, near N145C.

Physiological timing: Flowering commences mid-season in Motueka, New Zealand around the 5-15 January. Harvest is mid-season in the New Zealand season, commencing early to mid-March, under normal conditions.

Chemistry profile: 'Hort4337' has undergone extensive chemistry profile testing. 'Hort4337' has medium alpha acid levels around 10-12%, Beta acid levels around 4.5-5% and cohumulone levels around 27-29%.

HPLC & oil composition (measured within 6 months of harvest, stored at 0° C.):

| | |
|---|---|
| Alpha acids (HPLC) | 11% |
| Beta acids (HPLC) | 4.6% |
| Cohumulone content (% total alpha acids) | 27% |
| Total oils (mls/100 g) | 1.9% |
| A-Pinene, | 0% |
| B-Pinene, | 0.7% |
| Myrcene. | 60% |
| 2-methyl-butyl iso butyrate, | nt |
| Limonene, | 0.9% |
| Linalool, | 0.6% |
| Caryophyllene, | 4.6% |
| B-Ionone, | nt |
| Geraniol, | 0.9% |
| Nerol, | nt |
| Farnesene, | 0.1% |
| Humulene, | 17.3% |
| Citral, | nt |
| Geranyl Acetate, | 0.3% |
| Cilronellol | nt |

Where: nt = not measured

Use: Primarily flavouring and bittering ingredient for beer.

Pest and disease: 'Hort4337' does not appear particularly resistant or susceptible to any particular pests or diseases known to afflict *Humulus lupulus*.

Hardiness: The plant cold hardiness according to the American zone classification has not been determined.

The invention claimed is:

1. A new and distinct hop plant substantially as described and illustrated herein.

* * * * *